United States Patent [19]

Macovski

[11] Patent Number: 4,549,307
[45] Date of Patent: Oct. 22, 1985

[54] X-RAY IMAGING SYSTEM HAVING RADIATION SCATTER COMPENSATION AND METHOD

[75] Inventor: Albert Macovski, Menlo Park, Calif.

[73] Assignee: The Board of Trustees of The Leland Stanford, Junior University, Palo Alto, Calif.

[21] Appl. No.: 639,268

[22] Filed: Aug. 9, 1984

Related U.S. Application Data

[63] Continuation of Ser. No. 415,333, Sep. 7, 1982.

[51] Int. Cl.[4] .............................................. G03B 41/16
[52] U.S. Cl. ...................................... 378/145; 378/7; 378/99; 378/147
[58] Field of Search ..................... 378/145, 147, 7, 99

[56] References Cited

U.S. PATENT DOCUMENTS 4,286,156  8/1981  Wagner ................................. 378/7
4,380,818  4/1983  Pfeiler .................................. 378/99

Primary Examiner—Craig E. Church
Attorney, Agent, or Firm—Flehr, Hohbach, Test, Albritton & Herbert

[57] ABSTRACT

The image signal in a radiation imaging system is improved by establishing a scattered radiation signal and subtracting the scatter radiation signal from the detected radiation signal. The scatter radiation signal is established by shielding portions of the detector and measuring radiation at the shielded portions of the detector. The total scatter radiation signal is interpolated from spatial distribution of the radiation measured at the shielded areas.

6 Claims, 2 Drawing Figures

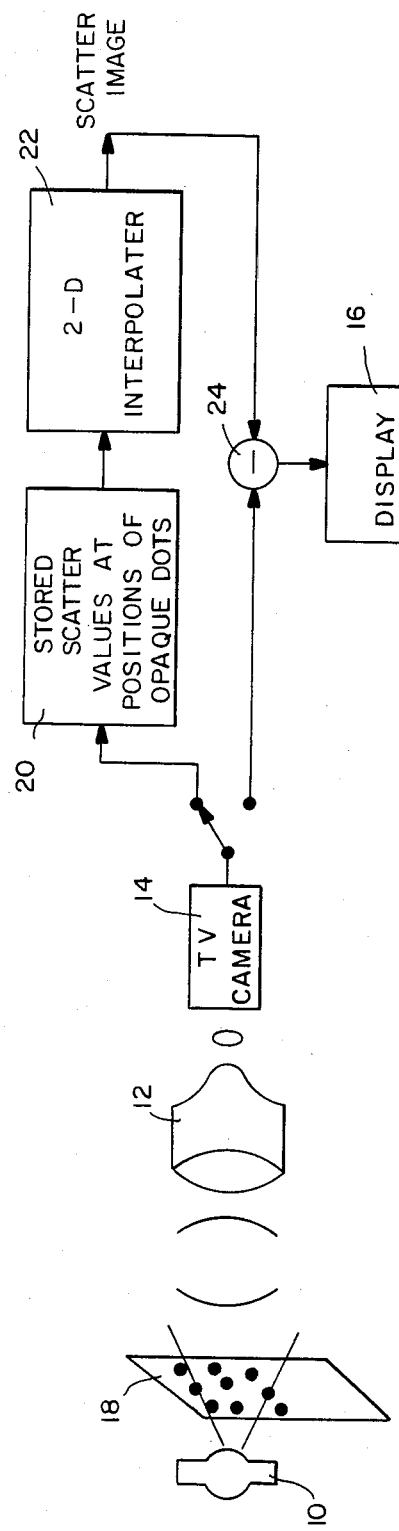
FIG.—1
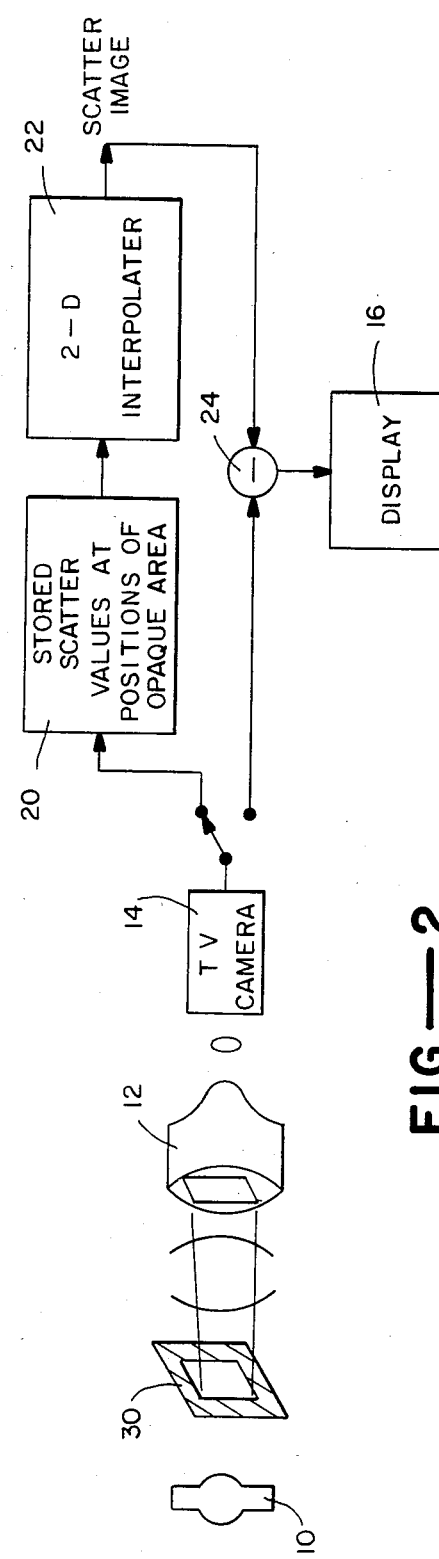
FIG.—2

X-RAY IMAGING SYSTEM HAVING RADIATION SCATTER COMPENSATION AND METHOD

This is a continuation of application Ser. No. 415,333 filed Sept. 7, 1982.

This invention relates generally to X-ray imaging systems, and more particularly the invention relates to a method of compensating such systems for radiation scatter and to the resulting system.

X-ray imaging systems are used for medical diagnostic purposes and for non-destructively inspecting the internal composition of various structures. A patient or specimen is irradiated by an X-ray beam and the elements of the specimen attenuate the radiation. A radiation-detector detects the attenuated radiation and generates an electrical signal indicative thereof. The electrical signal is then used to control a suitable monitor such as a TV receiver.

Radiation scatter is a significant source of error in all X-ray imaging systems employing area detectors. Fluoroscopic systems have an additional source of error due to optical scatter known as veiling glare. Energy selective imaging systems, such as dual energy systems, are particularly sensitive to scatter because of the subsequent processing.

Accordingly, an object of the present invention is a method of compensating for scatter in an X-ray imaging system.

Another object of the invention is an X-ray imaging system which compensates for radiation scatter.

A feature of the invention is the measurement of scattered radiation through use of an opaque shield placed in an imaging system whereby scattered radiation only is received by the shielded areas of the detector. The scattered radiation for the entire display can then be interpolated from the measured scattered radiation in the shielded areas of the detector.

Advantageously, the use of a shield for determining scattered radiation can be limited in area whereby scattered radiation is determined while the specimen is being imaged.

In one embodiment of an X-ray imaging system in accordance with the invention which utilizes a collimator for defining the X-ray beam pattern, a measurement of scattered radiation can be obtained by detecting the radiation in the area of the detector shielded by the collimator.

The invention and objects and features thereof will be more readily apparent from the following detailed description and appended claims when taken with the drawing, in which:

FIG. 1 is a functional block diagram of an X-ray imaging system having scatter compensation in accordance with the invention.

FIG. 2 is an alternative block diagram of an X-ray imaging system with scatter compensation in accordance with the invention.

Referring now to the drawing, FIG. 1 is a functional block diagram of an X-ray imaging system such as a fluoroscopic system in which X-radiation from a source 10 is directed through a specimen (not shown) to an image intensifier 12 such as scintillators which receive and intensifies the attenuated radiation passing through the specimen. Light from the intensifier 12 is received by TV camera 14 which generates a video signal. The intensifier and camera collectively form a radiation detector. The video signal from camera 14 is then applied to a display monitor 16 for viewing the internal structure of the specimen as determined by the attenuated radiation passing therethrough.

As above noted, radiation received by the image intensifier 12 includes a significant amount of scattered radiation which can cause a significant error in the displayed image. In accordance with the invention a measure of the scattered radiation is determined, and the video signal is then compensated by subtracting the measured scattered radiation. In the embodiment of FIG. 1 this is accomplished by providing an array 18 of X-ray opaque dots, for example, in the path between the X-ray source 10 and the image intensifier 12. Radiation received by the intensifier 12 aligned with the array of X-ray opaque dots will be solely scattered radiation since the direct passage of radiation is blocked by the opaque dots. Thus, the video signal of the detected radiation at the surfaces corresponding to the dot pattern is then stored in a memory 20. A two dimensional interpolator 22 then interpolates the scattered radiation across the entire surface of the detector 12 based on the geometric pattern of the X-ray opaque dots and the radiation measured at the corresponding positions on the surface of detector 12. The interpolated attenuation for the display is then subtracted at 24 from the video signal from camera 14 to provide a control signal for display 16 which is relatively free of error due to scatter.

The system as described with reference to FIG. 1 makes the basic assumption that the scatter is a low spatial frequency phenomena. Therefore, a relatively coarse set of samples of the scattered field will suffice to reconstruct the complete scatter distribution. The detected intensities at the positions corresponding to the opaque dots are recorded and used in the two dimensional interpolation arrangement to estimate the amount of veiling glare and scatter throughout the image plane. The estimated values are then subtracted from the measured intensities during the study.

The scatter calibration can be done with a fluoroscopic system by recording the values from the camera output corresponding to the position of the X-ray opaque dots. In other X-ray imaging systems, such as film systems, an array of detectors can be used in positions corresponding to the array of opaque dots to record the scatter. Alternatively, the film can be optically scanned with the values corresponding to the position of the opaque dots recorded and stored.

To provide a higher degree of sampling of the scatter field, an increased number of opaque dots can be used to provide greater accuracy. However, a relatively large number of dots will begin to substantially affect the amount of scatter produced. Accordingly, a predetermined weighting factor can be determined experimentally and applied to the measurements to account for the reduction of scatter.

In the case of a multiple energy system, stored scatter values are provided at each energy since the scatter is a function of energy. In some cases the scatter distribution at the different energies may differ only by a known constant weighting factor, therefore the scatter at a given energy level can be derived from a measurement at a different energy level.

FIG. 2 is a functional block diagram of an alternative embodiment similar to that of FIG. 1 but including a rectangular collimator 30 for limiting the field of the X-ray beam passing through a specimen. In this embodiment scattered radiation can be determined by measuring the radiation on the surface of the detector 12 corresponding to the surface of the collimator 30. The advantage of this embodiment is that the X-radiation passing through the specimen is not interrupted. However, the spatial distribution of the scatter may not be as accurate as that determined through use of X-ray opaque dots as in FIG. 1. In an alternative embodiment to that shown in FIG. 2 a limited number of opaque dots (such as used in FIG. 1) can be added to the system of FIG. 2 to more accurately estimate the spatial distribution of the scattered radiation.

The estimation and subtraction can be a one step or two step operation. In the one step operation the image of opaque dots are left in the final image since they are used to estimate the scatter. If these dots are found to be undesirable, a second image is taken with the array of dots 18 removed. As shown in FIG. 1, the switch is placed on position 2, with the scatter image subtracted from the camera signal, which is now free of dots. In this two step system the dots are removed at the price of increased radiation.

The number of dots required to accurately represent the scatter depends on the smoothness of the scattered radiation. This smoothness can be enhanced by separating the specimen from the detector, thus allowing the scattered radiation to spread and become more uniform. This will minimize the number of required dots so that they will become less objectionable when the one step system is used.

Through use of a scatter measurement and compensation system in accordance with the invention more accurate images can be developed of a specimen under examination. While the invention has been described with reference to a specific embodiment, the description is illustrative of the invention and is not to be construed as limiting the invention. Various modifications and applications may occur to those skilled in the art without departing from the true spirit and scope of the invention as defined by the appended claims.

What is claimed is:

1. A two-dimensional volumetric projection x-ray imaging system comprising
   an x-ray source,
   a two-dimensional x-ray detector means positioned to receive and detect x-radiation from said source and generate an electrical signal indication thereof,
   radiation shield means positioned between said source and an object being imaged and said detector means for shielding radiation from passing directly through the object to shielded areas of said detector means, said shield means comprising a plurality of radiation opaque bodies positioned between said source and the object being imaged and said detector means and spatially distributed within the imaging area of said detector means for facilitating two-dimensional interpolation of a scattered radiation signal for all of the detector means area,
   interpolation means for receiving electrical signals from said detector means indicative of scattered radiation received by said shielded area of said detector means and interpolating therefrom a scattered radiation signal for all of said detector means, and
   means for subtracting said interpolated scattered radiation signal from said electrical signal generated by said detector means.

2. The X-ray imaging system as defined by claim 1 wherein said shield means comprises a beam collimator for limiting the geometry of an X-ray beam received by said detector means directly from said source.

3. The X-ray imaging system as defined by claim 2 wherein said X-ray detector means comprises an image intensifier and a TV camera.

4. In a two-dimensional x-ray imaging system, a method of compensating for scatter radiation comprising the steps of
   positioning radiation shield means between the radiation source and an object being imaged and the radiation detector means within the imaging area thereby shielding a plurality of shielded area of said object and said radiation detector means within the imaging area,
   measuring radiation received by said radiation detector means at said shielded areas of said radiation detector means,
   interpolating scattered radiation for all of said detector means from the measured radiation at the shielded areas,
   measuring radiation received by said radiation means at all unshielded areas, and
   subtracting the interpolated scattered radiation from the measured x-radiation.

5. The method as defined by claim 4 wherein said steps of measuring radiation are concurrent.

6. The method as defined by claim 4 including the step of removing the radiation shield and measuring the radiation received at all areas.

* * * * *

UNITED STATES PATENT AND TRADEMARK OFFICE
CERTIFICATE OF CORRECTION

PATENT NO. : 4,549,307

DATED : October 22, 1985

INVENTOR(S) : ALBERT MACOVSKI

It is certified that error appears in the above-identified patent and that said Letters Patent is hereby corrected as shown below:

Column 1, line 5, after the title, insert the following paragraph:

--This invention was made with Government support under contract ECS78-23307 awarded by the National Science Foundation. The Government has certain rights in this invention.--

Signed and Sealed this

Ninth Day of May, 1995

*Attest:*

BRUCE LEHMAN

*Attesting Officer*     *Commissioner of Patents and Trademarks*